United States Patent
Wiley

(10) Patent No.: US 11,967,075 B2
(45) Date of Patent: *Apr. 23, 2024

(54) APPLICATION TO DETERMINE READING/WORKING DISTANCE

(71) Applicant: William F. Wiley, Chagrin Falls, OH (US)

(72) Inventor: William F. Wiley, Chagrin Falls, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 18/046,979

(22) Filed: Oct. 17, 2022

(65) Prior Publication Data

US 2023/0084867 A1    Mar. 16, 2023

Related U.S. Application Data

(63) Continuation of application No. 16/023,890, filed on Jun. 29, 2018, now Pat. No. 11,494,897.

(60) Provisional application No. 62/563,879, filed on Sep. 27, 2017, provisional application No. 62/529,530, filed on Jul. 7, 2017.

(51) Int. Cl.
*G06T 7/00* (2017.01)
*A61B 3/00* (2006.01)
(Continued)

(52) U.S. Cl.
CPC .......... *G06T 7/0012* (2013.01); *A61B 3/0041* (2013.01); *A61B 3/111* (2013.01);
(Continued)

(58) Field of Classification Search
CPC ........ G16H 10/60; G16H 50/20; G16H 50/30; G16H 80/00; A61B 3/0025; A61B 3/032; A61B 3/113; A61B 3/0041; A61B 3/112
See application file for complete search history.

(56) References Cited

U.S. PATENT DOCUMENTS

| 6,595,641 B1 | 7/2003 | Braeuning et al. |
| 2009/0079937 A1 | 3/2009 | Ying-Ling |

(Continued)

FOREIGN PATENT DOCUMENTS

| JP | 2004337546 A | 12/2004 |
| WO | WO 2016/083094 A1 | 6/2016 |
| WO | WO 2016/179370 A1 | 11/2016 |

OTHER PUBLICATIONS

Supplemental European Search Report for European Application No. 18828608.2 dated Feb. 18, 2021, 9 pages.

(Continued)

*Primary Examiner* — Margaret G Mastrodonato
(74) *Attorney, Agent, or Firm* — DeWitt LLP

(57) ABSTRACT

A method of measuring working distance between a handheld digital device and eyes of a user, including capturing an image of at least eyes of a user via an onboard camera of the handheld digital device while the user is viewing a display of the handheld digital device and comparing an apparent angular size of a structure of the eyes or face of the user to a previously captured image of the structure of the eyes or the face that was taken in the presence of an object of known size. The method further includes calculating a working distance based on the apparent angular size of the structure of the eyes or the face; and saving at least the working distance to memory or reporting out the calculated working distance on the display. A handheld digital device programmed with an algorithm to perform the method is also included.

21 Claims, 5 Drawing Sheets

(51) Int. Cl.

| | | |
|---|---|---|
| *A61B 3/11* | (2006.01) | |
| *A61B 3/113* | (2006.01) | |
| *G06T 7/20* | (2017.01) | |
| *G06T 7/521* | (2017.01) | |
| *G06T 7/62* | (2017.01) | |
| *G06T 7/73* | (2017.01) | |
| *G16H 10/60* | (2018.01) | |
| *G16H 30/20* | (2018.01) | |
| *G16H 30/40* | (2018.01) | |
| *G16H 40/63* | (2018.01) | |
| *G16H 80/00* | (2018.01) | |

(52) U.S. Cl.
CPC .............. *A61B 3/112* (2013.01); *A61B 3/113* (2013.01); *G06T 7/20* (2013.01); *G06T 7/521* (2017.01); *G06T 7/62* (2017.01); *G06T 7/74* (2017.01); *G16H 10/60* (2018.01); *G16H 30/20* (2018.01); *G16H 30/40* (2018.01); *G16H 40/63* (2018.01); *G16H 80/00* (2018.01); *G06T 2207/10024* (2013.01); *G06T 2207/30041* (2013.01); *G06T 2207/30201* (2013.01)

(56) References Cited

U.S. PATENT DOCUMENTS

| | | |
|---|---|---|
| 2012/0033227 A1 | 2/2012 | Bower |
| 2012/0262477 A1 | 10/2012 | Buchheit |
| 2012/0320340 A1 | 12/2012 | Coleman, III |
| 2013/0002722 A1 | 1/2013 | Krimon et al. |
| 2013/0235346 A1 | 9/2013 | Huang |
| 2014/0285436 A1* | 9/2014 | Wu ...................... A61B 5/1075 345/156 |
| 2014/0293219 A1 | 10/2014 | Haddadi et al. |
| 2014/0350379 A1 | 11/2014 | Verdooner |
| 2014/0375954 A1* | 12/2014 | Berry .................. G06F 9/44505 600/300 |
| 2016/0051145 A1 | 2/2016 | Rickard et al. |
| 2016/0083094 A1 | 3/2016 | Clucas et al. |
| 2016/0262608 A1* | 9/2016 | Krueger ................. G16H 40/63 |
| 2016/0309998 A1* | 10/2016 | Gonzalez Garcia .... A61B 3/111 |
| 2017/0003519 A1 | 1/2017 | Burkert et al. |
| 2017/0112373 A1* | 4/2017 | Burns .................. A61B 3/0058 |
| 2017/0156585 A1* | 6/2017 | Nie ........................ A61B 3/085 |
| 2017/0258319 A1* | 9/2017 | Weffers-albu ......... A61B 3/145 |
| 2018/0199810 A1 | 7/2018 | Li |
| 2019/0246896 A1* | 8/2019 | Hernandez-Castaneda ................. A61B 3/028 |

OTHER PUBLICATIONS

PCT International Preliminary Report on Patentability and Written Opinion for International Application No. PCT/US0218/040843, dated Jan. 16, 2020, 8 pages.

PCT International Search Report and Written Opinion for International Application No. PCT/US2018/040843, dated Nov. 16, 2018, 9 pages.

Application and File History for U.S. Appl. No. 16/023,890, filed Jun. 29, 2018. Inventor: William F. Wiley.

* cited by examiner

APPLICATION TO DETERMINE READING/WORKING DISTANCE

CROSS-REFERENCE TO RELATED APPLICATIONS

The present application is a continuation of U.S. application Ser. No. 16/023,890, filed Jun. 29, 2018, entitled "Application to Determine Reading/Working Distance", which claims benefit of U.S. Provisional Application No. 62/563,879, filed Sep. 27, 2017, entitled "Application to Determine Reading/Working Distance", and U.S. Provisional Application No. 62/529,530, filed Jul. 7, 2017, entitled "Application to Determine Reading/Working Distance," both of which are hereby incorporated in their entirety by reference.

TECHNICAL FIELD

Embodiments of the invention generally relate to the field of measuring distances in the context of eye care. More particularly, embodiments of the invention relate to monitoring reading ability of eye care patients.

BACKGROUND

Near working distance is a measurement from the eyes of an individual to material that they are reading or viewing at near distances. It comes into play, for example, in the context of reading a book, a newspaper or the screen of a handheld digital device. For example, near working distance is commonly measured in a clinical circumstance by asking a patient to hold in their hand and read a near point card which has on it printed letters of known sizes and requiring known visual acuity.

Measurement of near working distance and near visual acuity can provide valuable information that is useful in determining how effectively an individual is able to focus on and read printed material or view other images. Near working distance can give an indication of how successfully an individual is able to read or perceive materials viewed at near.

Personal computers and handheld digital devices are more and more often used for the reading of materials instead of conventional materials printed on paper. It is also the case that many personal computers and handheld digital devices such as smart phones, tablets, laptop computers and desktop computers now include a camera as part of their structure. Many of the cameras that are present include some form of autofocus mechanism and are capable of capturing both still and moving images.

Accommodation is the act of focusing from distance to near. In youth accommodation is very flexible and permits individuals to focus on near objects with minimal effort. Generally accommodation happens so automatically that people are entirely unaware of it. Conventional intraocular lens implants are generally provided in a prescription that focuses the patient's eye for clear distance vision. Generally reading glasses or other lenses are then used for near vision. While alternative approaches such as the monovision technique are available they are less than ideal and are successful only for some patients.

Intraocular lens implants that are utilized to provide corrective focusing after the natural lens is removed during cataract surgery now often include so-called accommodating or near vision intraocular lens implants. Through a variety of mechanisms these implants seek to provide assistance to patients when shifting vision from distance to near that attempt to emulate the natural focusing mechanism that exists in the youthful eye.

Accordingly there is still room for improvement in the eye care arts as to measuring working distance in real-life situations.

SUMMARY

Embodiments of the invention assist in providing useful clinical information to eye care practitioners by providing a way of unobtrusively monitoring the near working distance that a patient is actually using and providing information to the eye care practitioner by a variety of communication options.

An example embodiment of the invention includes a method of measuring working distance including calibrating by capturing an image of a user's face with an object of known size. The method further includes utilizing the known size of the object to calculate a relative size of structures of the face or eyes. The method also includes utilizing the known size of the object to calculate a distance between the camera of the handheld digital device and the patient eyes based on the known size of the object.

The example method also includes utilizing the calculated size of the structures of the face or eyes to determine a distance between the camera of the handheld digital device and the eyes of the patient while the patient is reading or viewing materials that are displayed on the handheld digital device. The method further includes monitoring the letter size of materials read on the handheld digital device display and includes storing in memory the calculated working distance along with the letter size of the materials read in a memory.

According to another example embodiment, the method further includes transmitting data to the health care professional from the handheld digital device including the working distance and letter size of the materials read. The method may also include calculating Snellen acuity or another acuity equivalent based on the working distance and the size of the materials read. Snellen acuity in this context is expected to be approximate as normal reading fonts do not necessarily comply with the Snellen equivalent for visual acuity. The method may also include transmitting the Snellen acuity and working distance to the health care practitioner for review.

The method according to an example embodiment of the invention may also include identifying from a captured image whether the user is wearing glasses or not when viewing the display on the handheld digital device. This information may be recorded and/or transmitted to the health care practitioner.

A handheld digital device according to example embodiments of the invention includes, for example, a smart phone or a tablet. Embodiments the invention may also utilize a laptop computer or desktop computer.

A handheld digital device according to an example embodiment of the invention generally includes a display, a camera module, a processor and a memory.

According to another example embodiment of the invention the processor of the handheld device is programmed with an algorithm that includes an image capture engine and an image analysis engine. The image capture engine includes computer code to be run by the processor that captures images for calibration and also captures images for measurement via a camera that is incorporated into the digital device.

The image analysis engine functions to analyze captured images both for the purposes of calibration and the purposes of measurement as well as analyzing images, for example, to determine whether glasses are worn at the time of reading.

According to another example embodiment, in the context of calibration an image is captured by the image capture engine of the face and eyes of a user along with an object of known size. For example, a credit card may be held in front of the forehead of the user since a credit card is of a known and standardized size. Another object of standardized size can be utilized as well. The image analysis engine is utilized to identify the object of known and standardized size as well as to identify structures of the face and/or eyes of the user in the captured digital image. For example, the white to white distance of one or both eyes can be used. The white to white distance is commonly understood to be analogous to the horizontal visible iris diameter (HVID). That is the distance across the cornea and iris and between the sclera of the eye on either side of the cornea.

The image analysis engine, according to an example embodiment further comprises a calculation engine that mathematically compares the apparent size of the known object to the apparent size of the white to white distance in the digital image to determine the white to white distance of one or both eyes. The white to white distance is then available for use to calculate the working distance between the handheld device and the eye at any given time because the apparent angular size of the white to white distance as captured by an image from the camera of the handheld device will vary depending upon the working distance between the device and the eye. White to white distance is used as an example here but should not be considered limiting. Other eye or facial structures may be utilized as well.

In the context of measurement, an image is captured of the eye and facial structures while the user is viewing or reading material on the display of the handheld device. According to an example embodiment of the invention, the image analysis engine determines the apparent angular size of the eye or facial structures, for example, the white to white distance of one or both eyes. The image analysis engine then can calculate the working distance between the handheld device and the eyes based on the apparent size of the structures in the captured image.

Optionally, according to an example embodiment, the image analysis engine can analyze the image displayed on the display of the handheld device to determine the font size of letters that are presented on the display. With the known working distance and the known font size of letters the image analysis engine can then calculate the visual acuity associated with the working distance and the letter size. The determination of visual acuity is based on the angular size of letters read and can be correlated to Snellen visual acuity which is known to those of skill in the art. Further for example, the image analysis engine can analyze the brightness of the image displayed on the display of the handheld device, the ambient brightness of ambient light or a combination of both.

The image analysis engine then can store the working distance along with identifying factors such as time and date in a memory the handheld device. Alternately, the image analysis engine can store the Snellen visual acuity along with identifying factors such as time, date and even location. The image analysis engine may also determine and record some indication of ambient lighting conditions at the time of reading and image capture as well as brightness of the display at the time of reading and image capture. Ambient light and brightness of the display may both affect the near vision function.

According to another example embodiment, stored measurements can be transmitted to a health care professional via the Internet, via wired connection or wireless connection. Alternately, measurements can be transmitted as soon as they are made.

A number of eye related circumstances present situations that may make it valuable to track working distance as an indication of near vision function. For example, such information may be valuable in patients utilizing monovision and patients who have undergone LASIK or other refractive surgery as well as patients with corneal inlays to assist with near vision. Further, it may be useful to track near vision in a normal patient approaching presbyopia and to provide information as to the onset of near focusing difficulties. Application of various embodiments of the invention may be utilized, for example, for patients who are approaching presbyopia to monitor their working distance and near vision status. Embodiments of the invention function to notify a surgeon or another eye care practitioner that working distance is increasing for the patient and, therefore, the patient may be needing assistance for near focusing because of presbyopia.

According to a further example embodiment, the handheld digital device can present a moving image similar to that of an optokinetic drum or optokinetic tape. These devices present a moving image of stripes, bars or checker boards that elicit optokinetic nystagmus in normally responsive eyes and visual systems. The evaluation of optokinetic nystagmus is useful for evaluation of neurological, otological or ophthalmological disorders. This embodiment may also include the image analysis engine tracking of eye movements in response to the optokinetic stimulus as well as saving of this information and transmission of this information to a health care practitioner. According to embodiments of the invention, the device can be adapted to present the optokinetic stimulus from left to right, right to left, top to bottom or bottom to top. Alternately, the device can be adapted to present the optokinetic stimulus in a single direction and provide instructions to the user to orient the handheld digital device in and appropriate orientation to direct the stimulus as desired. As a complement to the other near vision assessment performed by the device, the optokinetic stimuli may be presented with different bar widths and spacing to assist in evaluation of near visual acuity and near visual function.

According to another example embodiment, distance from the handheld digital device to the eye is measured by a depth mapping process using projected patterns. According to this example embodiment, a method for mapping includes projecting a pattern of multiple spots onto the face of the viewer. The multiple spots have respective positions and shapes and the positions of the spots in the pattern are uncorrelated, while the shapes share a common characteristic. Information about the size and spatial distortion of the multiple spots is gathered and used together to determine information about the depth or distance between the camera of the handheld digital device and the face. An image of the spots on the face is captured and processed so as to derive a three-dimensional map of the face from which a depth or distance to the eyes can be determined. According to this example embodiment the projected pattern may include a laser speckle pattern. According to this technique, a pixel image includes pixels that represent a depth or distance between the handheld digital device and the face rather than brightness or color. Application of this example embodiment takes advantage of hardware and software incorporated into at least some handheld digital devices that is also used for facial recognition.

According to another example embodiment of the invention, a depth map is created of the scene containing a face of a human user of the handheld digital device. The depth map includes a matrix of pixels. Each pixel corresponds to respective location in the scene and includes a respective pixel value indicative of a distance from a reference location at the handheld digital device to the respective location of the pixel. The depth map can be segmented to identify a contour of the face representing the eyes or bridge of the nose which can then be processed to identify the eyes or the bridge of the nose to identify a distance between the eyes or the bridge of the nose and the handheld digital device. Information related to such an embodiment can be found in U.S. Pat. No. 8,249,334 as well as U.S. Pat. No. 8,050,461, each of which is incorporated herein by reference.

According to another embodiment of the invention, the handheld digital device may include an apparatus for 3-D mapping of the face that includes an illumination assembly having a coherent light source and the diffuser which are arranged to project a speckle pattern on the face. Then, a single image capture assembly, such as the selfie, the camera on a cell phone or other handheld digital device can capture images of the primary speckle pattern with an infrared sensor from a single, fixed location and at a known angular position relative to the illumination source. The processor of the handheld digital device is programmed with an algorithm to process images of the speckle pattern to derive a 3-D depth map of the face. This then can be utilized to identify the distance between the handheld digital device and desired structures of the face such as the eyes or the bridge of the nose. Aspects of such a device are described in U.S. Pat. No. 8,390,821 which is incorporated herein by reference.

According to another example embodiment, a handheld digital device includes an illumination unit and an imaging unit. The illumination unit is structured to emit coherent light and to generate a random speckle pattern that is projected onto the face of the user of the handheld digital device. The imaging unit captures image data related to the face of the user and the random speckle pattern. The image data then is used to identify desired structures of the face such as the eyes or the bridge of the nose and to determine a distance between the handheld digital device and the structures. This then, enables determination of the working distance between the handheld digital device and the user's eyes.

The data processor of the handheld digital device may include a first input port the receives color image data and thus including a first array of color image pixels from the first image sensor as well as a second input port that receives depth related image data from a second image sensor as well as processing circuitry that generates a depth map using the depth related image data. The depth map can be further processed to identify structures of the eyes or bridge of the nose of the face and to determine a working distance between the handheld digital device and the eyes or bridge of the nose of the user. U.S. Pat. No. 8,456,517 which is incorporated by reference herein describes aspects of such a device.

According to another embodiment, the handheld digital device may perform a method of processing data including receiving a temporal sequence of depth maps of the scene including the face and using at least one of the depth maps to determine the location of the eyes or bridge of the nose and estimating distance between the handheld digital device and the eyes or the bridge of the nose. U.S. Pat. No. 8,565,479 is incorporated herein by reference.

According to another embodiment, the handheld digital device incorporates an illumination assembly that projects a speckle pattern of monochromatic light, for example, in the infrared wavelengths on to the face of a user. A processor of the handheld digital device is configured and adapted to process signals to generate an output a depth map of the face which then can be used to identify the eyes or bridge of the nose in order to determine a working distance between the handheld digital device and the user's eyes.

The following United States patents relate to embodiments of the invention and are hereby incorporated by reference. U.S. Pat. Nos. 8,582,867; 8,594,425; 8,717,417; and 8,749,796; 8,781,217; 8,786,682; 8,787, 663; 8,824, 737; 8,824,781; 8,848,039; and 8,872,762.

The above summary is not intended to describe each illustrated embodiment or every implementation of the subject matter hereof. The figures and the detailed description that follow more particularly exemplify various embodiments.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1:
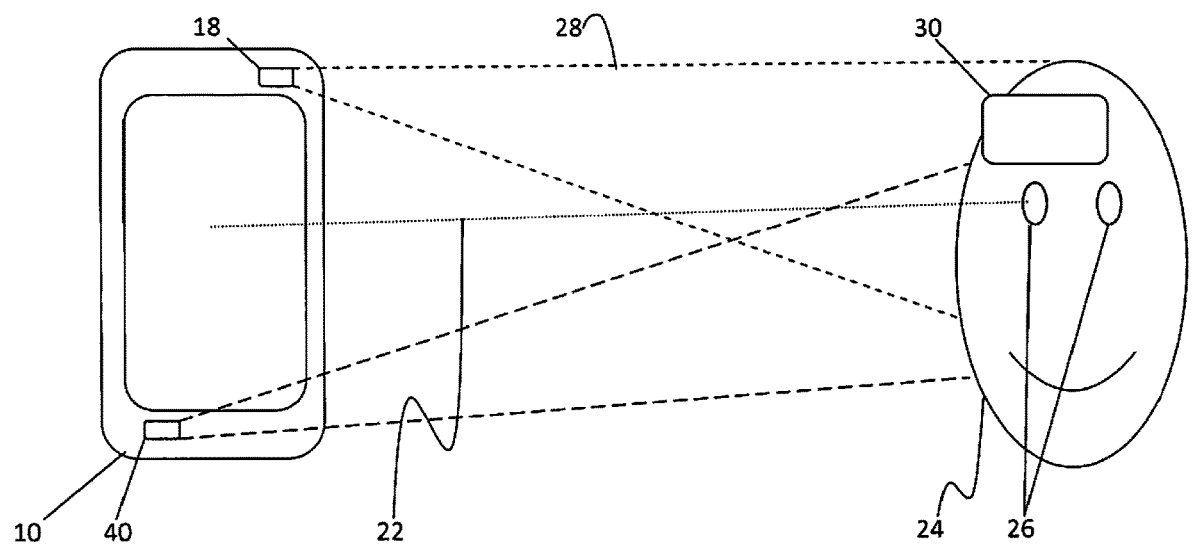
FIG. 1 is a schematic depiction of a digital handheld device and user according to an example embodiment of the invention.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Referring to FIGS. 1-4, example embodiments of the invention generally include a handheld digital device 10 programmed with an algorithm for use of the invention, and a method of measuring working distance between the handheld digital device and the eyes of a user viewing the device.

Figure 3:
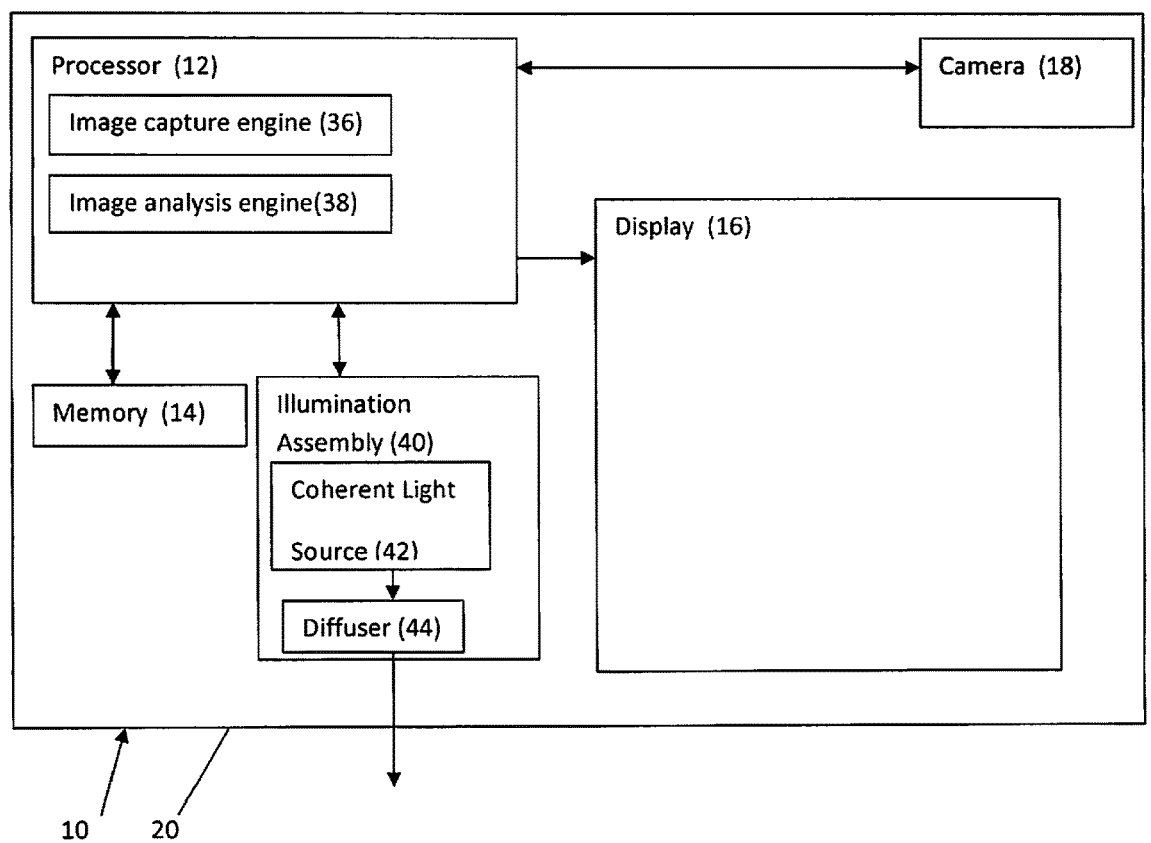
FIG. 3 is a schematic block diagram of a handheld digital device according to an example embodiment of the invention.

Referring particularly to FIG. 3, handheld digital device 10 generally includes processor 12, memory 14, display 16 and camera 18. Generally, processor 12 and memory 14 are provided within body 20 of handheld device digital device 10. Display 16 generally appears on at least one outer surface of handheld digital device 10. Many handheld digital devices 10 include camera 18 that faces a user when the user is viewing display 16. Thus, camera 18 permits the capturing of an image of the user while the user is viewing the display 16.

Referring particularly to FIG. 1, handheld digital device 10 is held at working distance 22 from patient's face 24 and eyes 26 when in use. For example, when reading text on display 16 of handheld digital device 10 working distance 22 is generally considered to be the distance of from display 16 to the anterior surface of eyes 26. Working distance 22 varies dependent upon many factors including an individual's arm length and ability to focus on near objects. Generally, most individuals will increase working distance 22 when they are having difficulty reaching due to limitations of accommodation. Field-of-view 28 of camera 18, according to an example embodiment, includes eyes 26 and at least part of face 24. Object of known size 30 can be presented within field of view 28 to be captured in an image by camera 18 along with at least part of face 24 and eyes 26. Object of known size 30 can include, for example, a credit card or other readily available object that has a known and standardized size.

Figure 2:
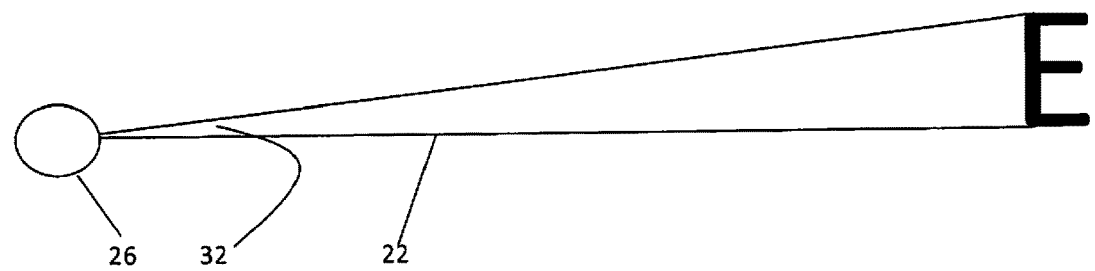
FIG. 2 is a schematic depiction of angular size is related to visual acuity according to the prior art.

Referring particularly to FIG. 2, visual acuity, as known in the prior art relates to apparent angular size 32 of a viewed object, in this case letter 34 at eye 26. As can be seen by reference to FIG. 2 and as is known to those skilled in the art, readability of text depends both on a size of letter 34 and working distance 22 from eye 26 to letter 34.

According to another example embodiment of the invention, camera 18 includes an autofocus mechanism which as part of its autofocus function determines a distance from camera 18 to an object to be photographed, in this case eyes 26. In this example embodiment, working distance 22 can be determined directly from the autofocus measured distance.

According to another example embodiment of the invention, a method of determining working distance 22 between a digital device 10 and eyes 26 is utilized. According to the example method, as depicted in the flow chart of FIG. 4, object of known size 30 is placed in front of or near face 24. Notably, object of known size 30 is not placed in front of eyes 26.

Processor 12 of digital device 10 comprises image capture engine 36 and image analysis engine 38. Image capture engine 36 is programmed with an algorithm to perform image capture functions discussed herein. Image analysis engine 38 is programmed with an algorithm to perform image analysis and calculation functions as described herein. Image capture engine 36 and image analysis engine 38 together function to perform the methods according to embodiments of the invention.

An example embodiment includes placing object of known size 30 in front of or near face 24 for calibration. The method further includes capturing an image of eyes 26 and/or face 24 as well as object of known size 30 with camera 18 of handheld digital device 10 by application of image capture engine 36. Image analysis engine 38 is then utilized to analyze features of the captured image. The relative size of ocular or facial structures is determined relative to the object of known size 30. For example the white to white distance of the eye can be determined. Also, working distance 22 between camera 18 and object of known size 30 can be determined by geometric calculation based on the apparent angular size of object of known size 30. Such geometric calculations are known in the field of geometric optics. Thus, based on future image captures working distance 22 can be calculated by image analysis engine 38 based on apparent angular size 32 of ocular structures, such as eyes 26, in captured images. This completes the calibration of image analysis engine 38 as regards working distance and apparent angular size 32 of structure of eyes 26.

Handheld digital device 10 is commonly used to read or view text such as news reports, blogs, email messages and text messages. Example embodiments of the invention are utilized to measure working distance 22 between handheld digital device 10 and eyes 26. Working distance 22 utilized by an individual provides an indication of how successfully and comfortably a user is able to read text on display 16 of handheld digital device 10. If a user is capable of reading displayed text at a working distance that is typical, for example 40 to 50 cm it would generally be accepted that the user is functioning well as to near focusing. If however, a user finds it necessary to move handheld digital device 10 to a greater working distance, for example 70 cm, it is suggestive that the user is not functioning well as to near focusing.

Accordingly, example embodiments of the invention enable monitoring of working distance 22 while the user goes about their normal day-to-day digital activities using handheld digital device 10. To assist in accomplishing this image capture engine 36 captures an image of face 24 and eyes 26 of a user while the user is reading text displayed on display 16 or viewing other materials on display 16. Monitoring is accomplished by analyzing a captured image with image analysis engine 38. Accordingly, reading material is presented on display 16 of handheld digital device 10 while image analysis engine 38, optionally, captures and records a font size of text, if text is displayed.

Image capture engine 36 is then utilized to capture an image of face 24 and/or eyes 26 of the user. Image analysis engine 38 is then utilized to determine the apparent size of structures of face 24 or eyes 26 based on earlier calibration. Based on the apparent size of structures of face 24 and/or eyes 26, working distance 22 is calculated by image analysis engine 38. Calculated working distance 22 is then saved to memory 14 by image analysis engine 38. According to example embodiments of the invention, other data may be saved to memory 14 as well. For example, time, date, lighting conditions, apparent pupil size and whether the user is wearing glasses at the time of recording can be captured and saved. These additional data may be determined from features of handheld digital device 10 itself in the case of time and date. For other data information may be determined by operation of algorithms utilized by image analysis engine 38, for example, in the case of lighting conditions, ambient brightness, display brightness, apparent pupil size and whether the user is wearing glasses.

According to another example embodiment, distance from handheld digital device 10 to eyes 26 can be measured by a depth mapping process using projected patterns. According to this example embodiment, a method for mapping includes projecting an illuminated pattern of multiple spots onto face 24 of the viewer. The multiple spots have respective positions and shapes and positions of the spots in the pattern are uncorrelated, while the shapes share a common characteristic. Information about the size and spatial distortion of the multiple spots is gathered and used together to determine information about the depth or distance between camera 18 of the handheld digital device 10 and face 24. An image of the spots on face 24 is captured and processed so as to derive a three-dimensional map of face 24 from which a depth or distance to eyes 26 can be determined. According to this example embodiment, the projected pattern may include a laser speckle pattern. According to this technique a pixel image includes pixels that represent a depth or distance between handheld digital device 10 and face 24 rather than brightness or color. Application of this example embodiment, takes advantage of facial recognition hardware and software incorporated into at least some handheld digital devices 10 that is also used for facial recognition.

According to another example embodiment of the invention, a depth map is created of the scene containing face 24 of a human user of handheld digital device 10. The depth map includes a matrix of pixels. Each pixel corresponds to respective location on the face or in the scene and includes a respective pixel value indicative of a distance from a reference location at handheld digital device 10 to the respective location of the pixel. The depth map can be segmented to identify a contour of face 24 representing eyes 26 or the bridge of the nose, for example, which can then be processed to identify eyes 26 or the bridge of the nose to determine a distance between eyes 24 or the bridge of the nose and handheld digital device 10.

According to another embodiment of the invention, handheld digital device 10 may include an apparatus for 3-D mapping of face 24 that includes illumination assembly 40 having coherent light source 42 and diffuser 44 which are arranged to project an illuminated speckle pattern on face 24. Then, a single image capture assembly, such as the selfie camera 18 on handheld digital device 10 captures images of the primary speckle pattern with an infrared sensor from a single, fixed location and at a known angular position relative to illumination assembly 40. Processor 12 of handheld digital device 10 is programmed with an algorithm to process images of the speckle pattern to derive a 3-D depth map of face 24. This can be utilized to determine or measure the distance between handheld digital device 10 and desired structures of face 24 such as eyes 26 or the bridge of the nose.

According to another example embodiment, handheld digital device 10 includes illumination assembly 40 and camera 18. Illumination assembly 40 is structured to emit coherent light and to generate a random speckle pattern that is projected onto face 24 of the user of handheld digital device 10. Image data then can be used to identify desired structures of face 24 such as eyes 26 and to determine a distance between handheld digital device 10 and eye 26 structures. This then enables determination of working distance 22 between handheld digital device 10 and user's eyes 26.

Processor 12 of handheld digital device 10 may include a first input port the receives color image data and thus including a first array of color image pixels from the first image sensor as well as a second input port that receives depth related image data from a second image sensor as well as processing circuitry that generates a depth map using the depth related image data. The depth map can be further processed to identify structures of eyes 26 or face 24 and to determine working distance 22 between the handheld digital device 10 and eyes 26 of the user.

According to another embodiment, handheld digital device 10 may perform a computer implemented method of processing data including receiving a temporal sequence of depth maps of the scene including face 24 and using at least one of the depth maps to determine the location of eyes 26 and estimating distance between handheld digital device 10 and eyes 26.

According to another example embodiment, handheld digital device 10 incorporates illumination assembly 40 that projects a speckle pattern of monochromatic light, for example, in the infrared wavelengths on to face 24 of a user. Processor 12 of handheld digital device 10 is configured and adapted to process signals to generate and output a depth map of face 24 which then can be used to identify eyes 26 to determine working distance 22 between handheld digital device 10 and the user's eyes 26.

According to example embodiments of the invention, data as to working distance may be captured periodically or each time handheld digital device 10 is viewed. Alternately, data as to working distance may be captured based on user activation of the future. Data related to working distance 22 is saved in memory 14 for download at the time of a user's next visit to a health care professional, for example. Alternatively, data related to working distance 22 can be sent via wired or wireless connection or via Internet connection to health care professional periodically.

According to another example embodiment of the invention, image analysis engine 38 can convert font size and measured working distance to Snellen visual acuity by calculations that are known to those skilled in the art. This information may also be later downloaded or periodically transmitted to a health care professional for analysis.

According to another example embodiment, image analysis engine 38 can determine and save data related to pupil size during the act of reading by a user. Pupil size may be recorded in correlation with working distance and/or font size and/or approximated Snellen visual acuity.

According to a further example embodiment, the handheld digital device 10 can present a moving image similar to that of an optokinetic drum or optokinetic tape on display 16. The moving image of stripes, bars or checker boards should elicit optokinetic nystagmus in normally responsive eyes and visual systems. The evaluation of optokinetic nystagmus is useful for evaluation of neurological, otological or ophthalmological disorders.

This embodiment may also include capturing of moving images of the eyes and any resulting optokinetic nystagmus and image analysis engine 38 tracking and analysis of eye movements in response to optokinetic stimulus as well as saving of this information to memory 14 and optionally, transmitting of this information to a health care practitioner.

According to embodiments of the invention, the handheld digital device 10 can be adapted to present the optokinetic stimulus on display 16 from left to right, right to left, top to bottom or bottom to top. Diagonal presentations can be presented as well. Alternately, handheld digital device 10 is adapted to present the optokinetic stimulus in a single direction and provide instructions to the user to orient handheld digital device 10 in an appropriate orientation to direct the stimulus as desired. As a complement to the other near vision assessment performed by the device, optokinetic stimuli may be presented with different bar widths and spacing to assist in evaluation of near visual acuity and near visual function.

Figure 4:
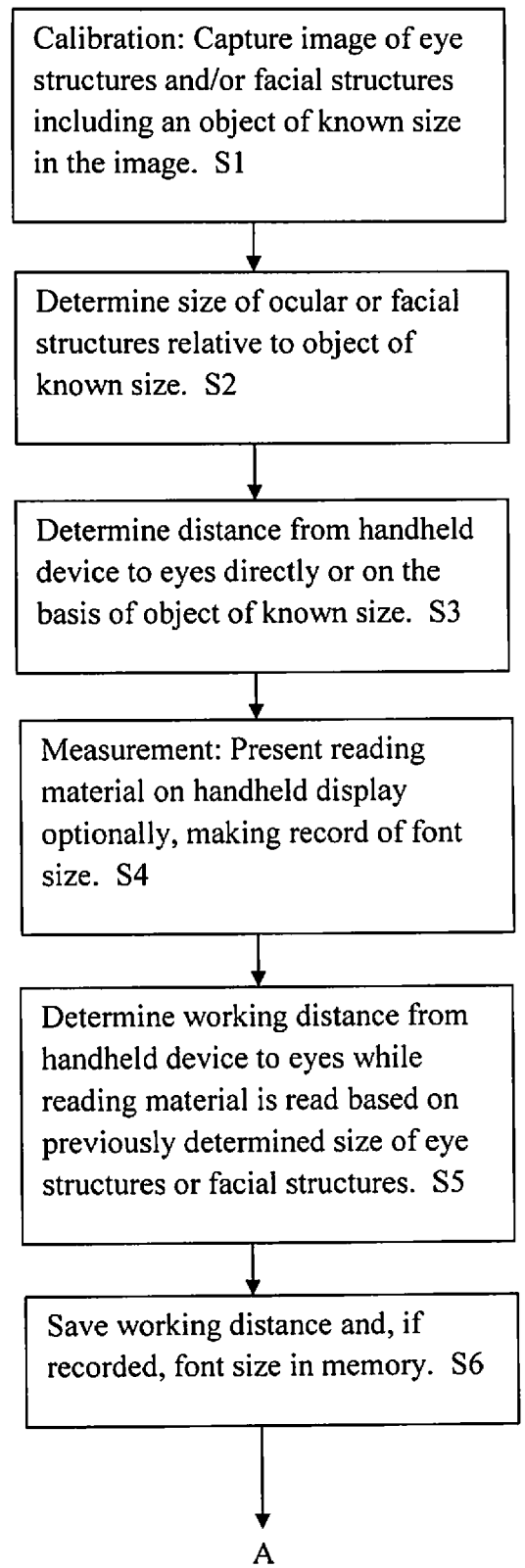
FIG. 4 is a flowchart depicting a method according to an example embodiment of the invention.
Figure 4:
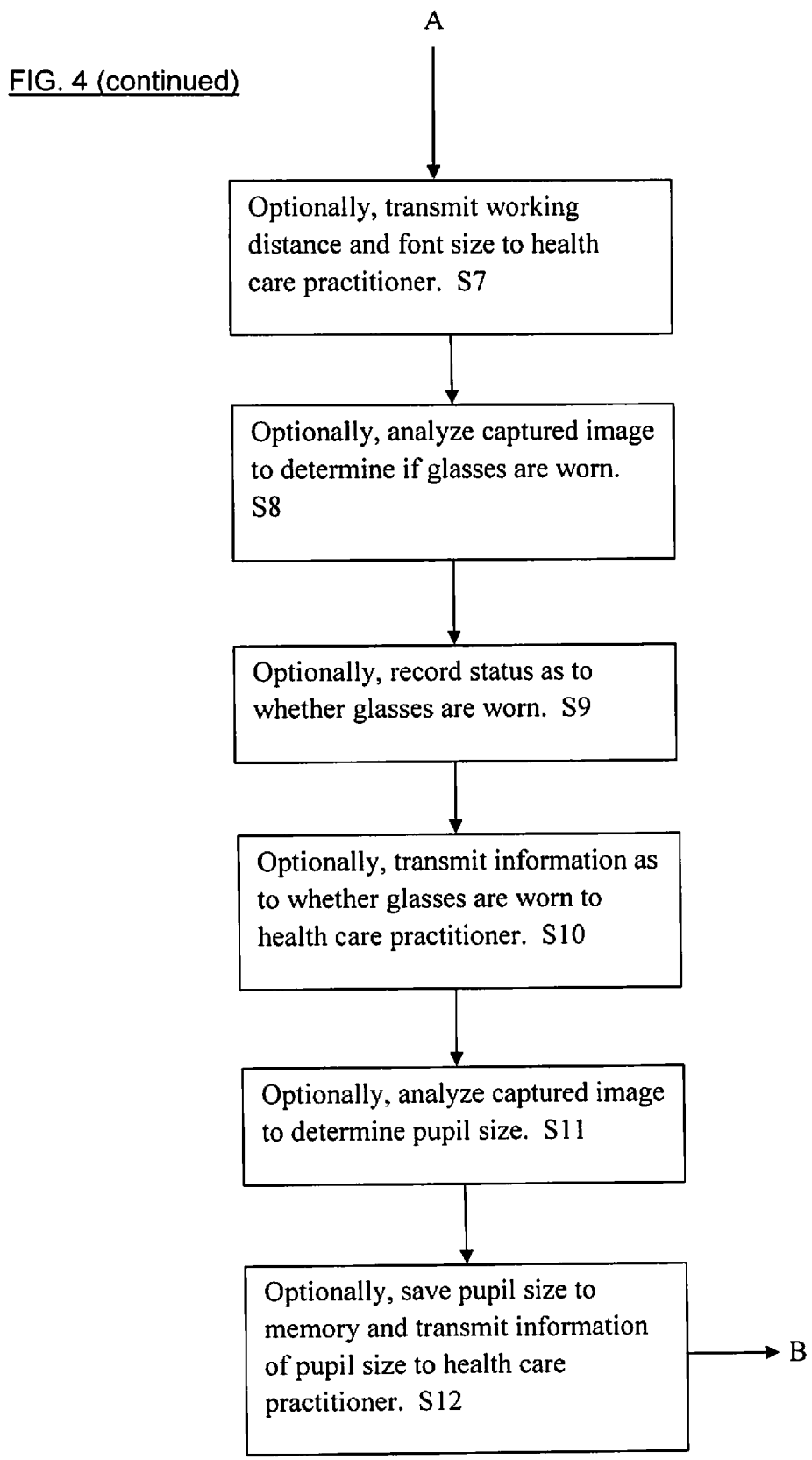
Figure 4:
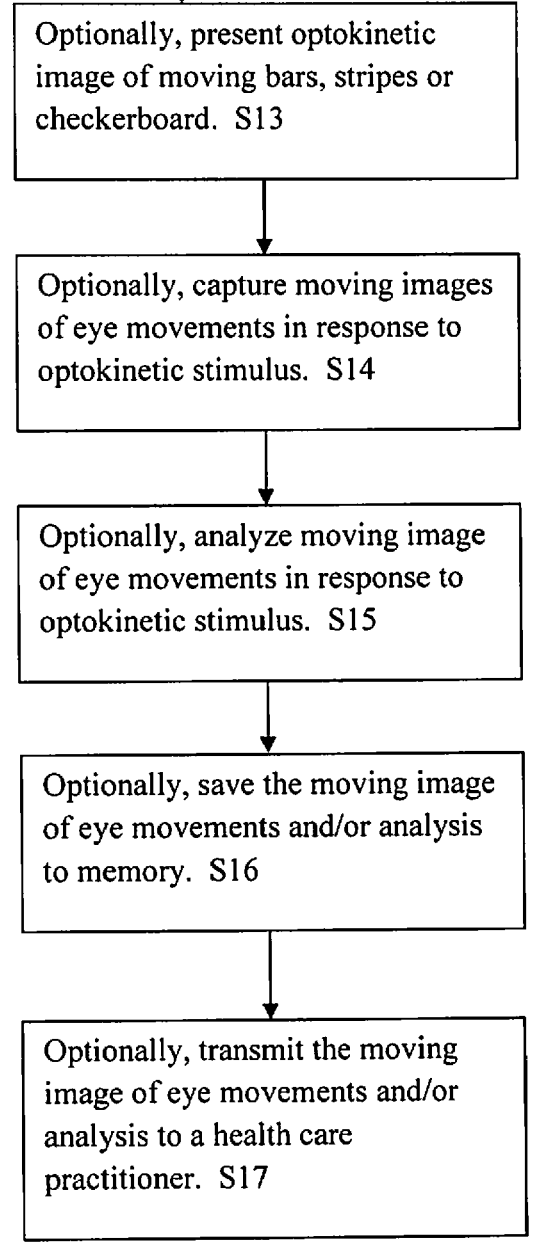

Referring particularly to FIG. 4, according to an example embodiment of a method calibration can be accomplished by capturing an image of an eye structures and/or facial structures including an object of known size in the image S1. Image analysis engine 38 can then be utilized to determine a size of ocular or facial structures of eyes 26 and/or face 24 relative to object of known size 30 S2. Working distance 22 may then be determined on the basis of object of known size S3. Calibration of the method is then complete.

Measurement can then proceed by presenting reading materials on a display 16 of handheld digital device 10 which are read by a user S4. Optionally, as part of S4 font size presented on the display can be determined and recorded. Image analysis engine can then determine working distance 22 from handheld digital device 10 to eyes 26 based on the previously determined size of the eye structures or facial structures of eyes 26 or face 24 S5. Image analysis engine 38 can then save working distance 22 and if recorded font size in memory 14 S6.

Optionally, image analysis engine 38 can transmit working distance 22 and font size if recorded to health care practitioner S7.

Further optionally, according to another example embodiment of the method, image analysis engine 38 may analyze a captured image to determine if glasses are worn on the face of a user S8. Image analysis engine 38 may then saved in memory 14 a status as to whether glasses are worn S9. Optionally, status or information as to whether glasses are worn can be transmitted to a health care practitioner via wired or wireless connection or Internet S10.

Further optionally, according to another example embodiment of the method, image analysis engine 38 may analyze a captured image to determine a pupil size S11. Image analysis engine 38 may further save information as to pupil size to memory and transmit information as to pupil size to a health care practitioner S12.

Further optionally, according to another example embodiment, an optokinetic image of moving bars stripes or a checkerboard may pre-presented on display 16 of handheld digital device 10. Image capture engine 36 then captures moving images of eye movements that occur in response to the optokinetic stimulus S14.

Optionally, image analysis engine 38 may analyze the moving image of eye movements in response to the optokinetic stimulus to determine whether the response is within normal limits S15.

Optionally, image analysis engine 38 may save the moving image of eye movements and/or the analysis of eye movements to memory 14 S16.

Further optionally, an example embodiment of the method may include transmitting the moving image of eye movements and/or analysis to a health care practitioner S17.

Further, according to another example embodiment of the method, image analysis engine 38 may analyze pupil size at various times during the act of reading. Pupil size may be correlated with working distance and/or font size and/or approximate Snellen visual acuity. Pupil size and its correlation with the above factors may assist in determining how well a particular treatment for presbyopia is working. It may be beneficial for the health care practitioner to know whether the treatment is working better when the pupil size is large or when the pupil size is small. Pupil size may also provide some indication of accommodative effort as it is known to those skilled in the art that pupil size may vary with accommodative effort. Generally, accommodation, convergence and pupil constriction tend to be linked. Pupil size also correlates with the level of illumination. It is known that the pupil constricts in brighter light conditions. Identification of inequality of pupil size between the two eyes may assist in the detection of pathology. Aniscoria (unequal pupil size) can be physiological or can be related to abnormalities in the optic nerve or in the other cranial nerves that innervate the eye.

A health care practitioner can then consider information as to working distance 22, font size and status as to whether glasses are worn or not as well as other considerations in evaluating a user or a patient's ability to function when utilizing near vision.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A computer implemented method of assessing visual function of a user, comprising:
providing a handheld digital device to the user, the handheld digital device including a display and a camera;
presenting an optokinetic stimulus to the user on the display of the handheld digital device;
monitoring eye movement of the user while the user views the optokinetic stimulus;
varying the optokinetic stimulus while monitoring the eye movements of the user;
measuring a working distance between the display and eyes of the user;
saving at least the working distance measured to memory, reporting out the working distance measured on the display or both;
making a record of parameters of the optokinetic stimulus on the display of the handheld digital device; and transmitting the working distance and the parameters of the optokinetic stimulus to a health care practitioner.

2. The computer implemented method as claimed in claim 1, further comprising presenting the optokinetic stimulus as a moving image of stripes, bars or checkerboards.

3. The computer implemented method as claimed in claim 1, further comprising presenting the optokinetic stimulus in varying directions on the display.

4. The computer implemented method as claimed in claim 1, further comprising presenting the optokinetic stimulus in a consistent direction on the display and presenting instructions to the user to hold the display in a desired orientation.

5. The computer implemented method as claimed in claim 1, further comprising presenting the optokinetic stimulus with varying width and spacing.

6. The computer implemented method as claimed in claim 1, further comprising calibrating a processor of the handheld digital device by capturing an image of eye structures, facial structures or both while including an object of known size in the captured image.

7. The computer implemented method as claimed in claim 6, further comprising measuring a size of the eye structures, facial structures or both relative to the object of known size in the captured image.

8. The computer implemented method as claimed in claim 7, further comprising recording status as to whether the corrective lenses are worn when the optokinetic stimulus is viewed and transmitting the status as to whether corrective lenses are a worn to the health care practitioner.

9. The computer implemented method as claimed in claim 1, further comprising measuring the working distance directly or on the basis of comparison to the object of known size.

10. The computer implemented method as claimed in claim 1, further comprising measuring the working distance while the optokinetic stimulus is viewed.

11. The computer implemented method as claimed in claim 1, further comprising saving additional information to memory selected from a group consisting of time, date, lighting conditions, display brightness, pupil size, whether the user is wearing corrective lenses at the time of recording and a combination of the foregoing.

12. The computer implemented method as claimed in claim 1, further comprising analyzing a captured image to determine a pupil size; and optionally, transmit information of the pupil size to a health care practitioner.

13. A handheld digital device, comprising:
a display;
a camera;
a processor; and
a memory;
wherein the processor is in operable communication with the display, the camera and the memory and further comprises an image capture engine and an image analysis engine;
the processor being programmed to present an optokinetic stimulus on the display of the handheld digital device;
the image capture engine being programmed to execute the following:
monitoring eye movement of a user while the user views the optokinetic stimulus;
varying the optokinetic stimulus while monitoring the eye movements of the user;
measuring a working distance between the display and eyes of the user;
saving at least the working distance measured to memory, reporting out the working distance measured on the display or both;
making a record of parameters of the optokinetic stimulus on the display of the handheld digital device; and
transmitting the working distance and the parameters of the optokinetic stimulus to a health care practitioner.

14. The handheld digital device as claimed in claim 13, wherein the processor is further programmed, to present the optokinetic stimulus as a moving image of stripes, bars or checkerboards.

15. The handheld digital device as claimed in claim 13, wherein the processor is further programmed, to present the optokinetic stimulus in varying directions on the display.

16. The handheld digital device as claimed in claim 13, wherein the processor is further programmed, to present the optokinetic stimulus in a consistent direction on the display and presenting instructions to the user to hold the display in a desired orientation.

17. The handheld digital device as claimed in claim 13, wherein the processor is further programmed, to present the optokinetic stimulus with varying width and spacing.

18. The handheld digital device as claimed in claim 13, wherein the processor is further programmed to save additional information to memory selected from a group consisting of time, date, lighting conditions, display brightness, pupil size, whether the user is wearing corrective lenses at the time of recording and a combination of the foregoing.

19. The handheld digital device as claimed in claim 13, wherein the processor is further programmed to record status as to whether the corrective lenses are worn when the optokinetic stimulus is viewed and transmitting the status as to whether corrective lenses are a worn to the health care practitioner.

20. The handheld digital device as claimed in claim 13, wherein the processor is further programmed to analyze a captured image to determine a pupil size; and optionally, transmit information of the pupil size to a health care practitioner.

21. A handheld digital device, comprising:
a display;
a camera;
a processor; and
a memory;
wherein the processor is in operable communication with the display, the camera and the memory and further comprises an image capture engine and an image analysis engine;
the processor being programmed to present a visual stimulus on the display of the handheld digital device;
the image capture engine being programmed to execute the following:
measuring a working distance between the display and eyes of the user;
saving at least the working distance measured to memory, reporting out the working distance measured on the display or both;
making a record of parameters of the visual stimulus on the display of the handheld digital device; and
transmitting the working distance and the parameters of the visual stimulus to a health care practitioner.

* * * * *